(12) United States Patent
Song et al.

(10) Patent No.: US 7,078,396 B2
(45) Date of Patent: Jul. 18, 2006

(54) METHOD OF TREATING DISORDER RELATED TO HIGH CHOLESTEROL CONCENTRATION

(75) Inventors: Ching Song, Chicago, IL (US); Shutsung Liao, Chicago, IL (US)

(73) Assignee: ARCH Development Corporation, Chicago, IL (US)

(\*) Notice: Subject to any disclaimer, the term of this patent is extended or adjusted under 35 U.S.C. 154(b) by 69 days.

(21) Appl. No.: 10/290,997

(22) Filed: Nov. 8, 2002

(65) Prior Publication Data

US 2003/0139385 A1 Jul. 24, 2003

Related U.S. Application Data

(63) Continuation-in-part of application No. 10/137,695, filed on May 2, 2002.

(60) Provisional application No. 60/348,019, filed on Nov. 8, 2001, provisional application No. 60/288,643, filed on May 3, 2001.

(51) Int. Cl.
*A61K 31/56* (2006.01)

(52) U.S. Cl. .................. 514/182; 514/824

(58) Field of Classification Search ............... 514/182, 514/824
See application file for complete search history.

(56) References Cited

U.S. PATENT DOCUMENTS

| | | | |
|---|---|---|---|
| 2,698,853 A | 1/1955 | Wildi ...................... 260/397.2 |
| 3,784,598 A | 1/1974 | Iseli et al. |
| 3,887,545 A | 6/1975 | Iacobelli et al. .... 260/239.55 R |
| 3,925,480 A | 12/1975 | Thal et al. |
| 3,963,765 A | 6/1976 | Mazur et al. ............ 260/397.2 |
| 4,006,172 A | 2/1977 | Salmond |
| 4,125,544 A | 11/1978 | Dygos |
| 4,193,930 A | 3/1980 | Chorvat .................. 260/397.2 |
| 4,304,726 A | 12/1981 | Arakawa et al. ........ 260/397.2 |
| 4,639,420 A | 1/1987 | Schaffner |
| 4,917,898 A | 4/1990 | Angelico et al. ........... 424/452 |
| 5,332,857 A * | 7/1994 | McCarthy et al. ........... 560/60 |
| 5,362,891 A | 11/1994 | Bonaldi et al. ............. 552/554 |
| 5,424,463 A | 6/1995 | Lardy et al. ............... 552/637 |
| 5,466,815 A | 11/1995 | Enhsen et al. .............. 548/252 |
| 5,482,935 A | 1/1996 | Adelman et al. |
| 5,508,453 A | 4/1996 | Arosio et al. .............. 552/553 |
| 5,562,910 A | 10/1996 | Daynes et al. ........... 424/278.1 |
| 5,583,239 A | 12/1996 | Regen ........................ 552/554 |
| 5,639,744 A | 6/1997 | Marchi et al. .............. 514/176 |
| 6,060,465 A | 5/2000 | Miljkovic et al. .......... 514/169 |
| 6,369,247 B1 | 4/2002 | Miller et al. ................ 552/542 |
| 6,465,258 B1 | 10/2002 | Shan et al. .................. 436/501 |
| 6,639,078 B1 | 10/2003 | Haffner et al. ........... 546/272.1 |
| 6,645,955 B1 | 11/2003 | Liao et al. .................. 514/182 |
| 2002/0107233 A1 | 8/2002 | Liao et al. .................. 514/182 |
| 2002/0193357 A1 | 12/2002 | Song et al. ................. 514/169 |
| 2004/0014734 A1 | 1/2004 | Song et al. ................. 514/169 |

FOREIGN PATENT DOCUMENTS

| | | |
|---|---|---|
| CN | 123 286388 | 3/1995 |
| CN | 110729 | 3/1995 |
| EP | 0 562 849 A2 | 9/1993 |
| GB | 1 405 818 | 9/1975 |
| GB | 2 009 180 | 6/1979 |
| WO | 94/02503 | 2/1994 |
| WO | 98/32444 | 7/1998 |
| WO | 00/66611 | 11/2000 |
| WO | 02/062302 | 8/2002 |
| WO | 02/090375 | 11/2002 |
| WO | 03/039480 | 5/2003 |
| WO | 03/086303 | 10/2003 |

OTHER PUBLICATIONS

Cohen-Solal et al., "Effects of hyodeoxycholic acid and alpha-hyocholic acid, two 6 alpha-hydroxylated bile acids, on cholesterol and bile acid metabolism in the hamster." Biochimica et biophysica Acta, vol. 1257, pp. 189-197, 1995.*

(Continued)

*Primary Examiner*—Barbara P. Badio
(74) *Attorney, Agent, or Firm*—Fish & Richardson P.C.

(57) ABSTRACT

A method of treating a disorder related to a high cholesterol concentration, comprising administering to a subject in need thereof a compound of formula (I):

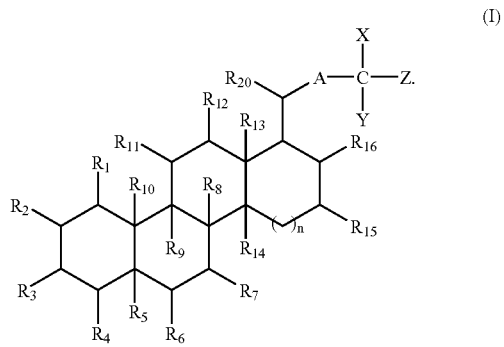

Also disclosed are methods, kits, combinations, and compositions for treating a disorder in a subject where an activator of liver X alpha is indicated, such as in, for example, treating a high cholesterol disease.

25 Claims, No Drawings

OTHER PUBLICATIONS

Angelico et al., Dissolution of Human Cholesterol Gallstones in Bile Salt/Lecithin Mixtures: Effect of Bile Salt Hydrophobicity and Various pHs, Scandinavin Journal of Gasteroenterology 30:1178-1185, 1195.

Bleau et al. "Cholesterol sulfate. I. Occurrence and possible biological function as an amphipathic lipid in the membrane of the human erythrocyte." Biochimica et Biophysica Acta, vol. 352(1), pp. 1-9, (1974).

Ajay Chawla et al., "Nuclear Receptors and Lipid Physiology: Opening the X-Files", Science, vol. 294, pp. 1866-1870 (Nov. 30, 2001).

Cohen et al., "The preparation of bile acid amides and oxazolines. II. The synthesis of the amides and oxazolines of ursdeoxycholic acid, deoxycholic acid, hyodeoxycholic acid and cholic acid", Steroids, vol. 40, No. 6, pp. 701-711 (Dec. 1982).

Coleman et al., "Synthesis and Characterization of Novel Analogs of Conjugated Bile Acids Containing Reversed Amide Bonds", Journal of Lipid Research 36:901-910, 1995.

Dusza et al., "A Fusion Method for Preparation of Steroid Sulfates," Steroids p. 317-323 (1985).

Dusza et al., "The Preparation of Estradiol-17β Sulfates with Triethylamine-Sulfur Trioxide," Steroids p. 303-315 (1985).

Adomo Fini et al., "Quantitative Structure-Antimicrobial Activity Relationship in 5β-Cholanyl-24-benzylamine Derivatives", Journal of Pharmaceutical Sciences, vol. 79, No. 7, pp. 603-605 (Jul. 1990).

Charles Freudenreich, et al., "Design of Inhibitors from the Three-Dimensional Structure of Alcohol Dehydrogenase, Chemical Synthesis and Enzymatic Properties", J. Am. Chem. Soc., pp. 3344-3353, (1984).

Xuan Fu et al., "27-Hydroxycholesterol Is an Endogenous Ligand for Liver X Receptor in Choleserol-loaded Cells", The Journal of Biological Chemistry, Vo. 276, No. 42, pp. 38378-38387 (2001).

Josef E. Herz, et al., "Fluorinated Sterols. Part II: 26,27—Polyfluorinated Desmosterols", Journal of Fluorine Chemistry, vol. 8, pp. 209-222 (1976).

Mohammed N. Iqbal, et al., "Bile Acids. LXXXI. Synthesis and structural assignment of E/Z isomers of substituted methyl hydroxy-5β-cholest-24-en-26-oates", Steroids, vol. 56, pp. 505-512 (Oct. 1991).

Janowski et al., "Structural Requirements of Ligands for the Oxysterol Liver X Receptor LXRα and LXRβ", Proc. Natl. Acad. Sci. vol. 96, pp. 266-271, (Jan. 1999).

Kim et al., "Inhibitors of Sterol Synthesis, Chemical Synthesis, Structure, and Biological Activities of (25R)-3β,26-dihydroxy-5α-cholest-8(14)-en-15-one, a Metabolite of 3β-hydroxy-5α-cholest-8(14)-en-15-one", Journal of Lipid Research 30:247-261, 1989.

Naoyuki Koizumi, et al., Synthesis of [25R]—and [25S]-25,26-Dihydroxyvitamin D31, Tetrahedron Letters, No. 32, pp. 2899-2902 (1978).

Kornel et al., "Studies on Steroid Conjugates: II Chemical Synthesis and Characterization of Sodium Cortisol-21-Sulfate and Sodium Tetrahydrocortisol-3, 21-Disulfate," Steroids. P. 67-75 (1964).

Kurosawa et al., "Synthesis of 3α, 7α, 12α-trihydroxy-and 3α, 7α-dihydroxy-5β-cholestan-26-oic Acids by the Use of β-ketosulfoxide", Steroids 60:439-444, 1995.

Bryan A. Laffitte, et al., "LXRs control lipid-inducible expression of the apolipoprotein E gene in macrophages and adipocytes", PNAS, vol. 98, pp. 507-512, (Jun. 16, 2001).

Yvonne Lange, et al., "Cholesterol Movement in Niemann-Pick Type C Cells and in Cells Treated with Amphiphiles", The Journal of Biological Chemistry, vol. 275, No. 23, pp. 17468-17475, (Jun. 9, 2000).

Dieter Leibfritz, et al., "Nuclear Magnetic Resonance Spectroscopy. Carbon-13 Spectra of Cholic Acids and Hydrocarbons Included in Sodium Desoxycholate Solutions", Journal of American Chemical Society, vol. 95, No. 14, pp. 4996-5003 (Jul. 11, 1973).

Li et al., "Sterol Synthesis. Preparation and Characterization of Fluorinated and Deuterated Analogs of Oxygenated Derivatives of Cholesterol", Chemistry and Physics of Lipids 99:33-71, 1999.

Nambara et al., "Preparation of Specific Antiserum to Estriol 3-Sulfate 16-Glucuronide," Journal of Steroid Biochemistry, 21: p. 199-203 (1984).

S.H. Mujtaba Naqvi, "Chemical Synthesis and Mass Spectrometric Characterization of Some C-27 Steroids", Steroids, vol. 22, pp. 285-290 (1973).

Roda et al., "Synthesis and Phsicochemical, Biological, and Pharmacological Properties of New Bile Acids Amidated with Cyclic Amino Acids", J. Med. Chem. 39:2270-2276, 1996.

Ruelle et al., "The Mobile Order Solubility Equation Applied to Polyfunctional Molecules: The Non-hydroxysteroids in Aqueous and Non Aqueous solvents", International Journal of Pharmaceutics 157:219-232, 1997.

Ching Song et al., "Auto-oxidized cholesterol sulfates are antagonistic ligands of liver X receptors: implications for the development and treatment of atherosclerosis", Steroids, vol. 66, pp. 473-479 (2001).

Song et al., "Cholestenioc Acid Is a naturally Occuring Ligand for Liver X Receptor α," Endocrinology, 141: p. 4180-4184 (2000).

Ching Song et al., "Hypolipidemic effects of selective liver X receptor alpha agonists", Steroids, vol. 66, pp. 673-671 (2001).

Song et al., "Selective Activation of Liver X Receptor Alpha by 6α-Hydroxy Bile Acids and Analogs," Steroids, 65: p. 423-427 (2000).

Song et al., "Ubiquitous Receptor: A Receptor that Modulates Gene Activation by Retinoic Acid and Thyroid Hormone Receptors", Proc. Natl. Acad. Sci. 91:10809-10813, 1994.

Song et al., "Ubiquitous Receptor: Structures, Immunocytochemical Localization, and Modulation of Gene Activation by Receptors for Retinoic Acids and Thyroid Hormones", Annals of the New York Academy of Sciences 761:38-49, 1995.

Sweeny et al., "Metabolism of 5-fluorouracil to an N-cholyl-2-fluoro-β-alanine conjugate: Previously Unrecognized Role for Bile Acids in Drug Conjugation", Proc. Natl. Acad. Sci. 84:5439-5443, 1987.

Summerfield et al., "Identification of Bile Acids in the Serum and Urine in Cholestasis", Biochem. J. 154:507-516, 1976.

Tanaka et al., "Specific Antisera for the Radioimmunoassay of Estradiol-3-Sulfate," Journal of Steroid Biochemistry, 22: p. 285-288 (1985).

Varma et al., "Synthesis and C-25 Chirality of 26-Hydroxycholesterols",The Journal of Organic Chemistry 40:3680-3686, 1975.

Wei et al., "Modulation of Hormone-dependent Glucocorticoid Receptor Function Using a Tetracycline-regulated Expression System", J. Steroid Biochem. Molec. Biol. 64:1-12, 1998.

Michael W. Whitehouse et al., "Catabolism in vitro of cholesterol: some comparative aspects", Arch. Biochem. Biophys., 98, pp. 305-311 (1962).

Xia et al., "Synthesis of N-Substituted 3-OXO-17β-Carboxamide-4-AZA-5α-Androstanes and the Tautomerism of 3-OXO-4-AZA-5-Androstenes", Heterocycles 47:703-716, 1998.

Stephen A. Ziller, Jr., et al., "Bile Acids. XXV. Allochenodeoxycholic Acid, A Metabolite of 5α-Cholestan-3β-OL in the Hyperthyroid Rat", The Journal of Biological Chemistry, vol. 243, pp. 5280-5288 (1968).

Bergmann et al., "Contribution to the study of marine products. XXXI. Palysterol and other lipid components of sea anemones", Journal of Organic Chemistry, 16:1337-1344 (1951).

Boto et al., "Tandem b-Fragmentation-hydrogen Abstraction Reaction of Alkoxy Radicals in Steroid Systems", Journal of Organic Chemistry, 62(9):2975-2981 (1997).

Database Beilstein Online!, Beilstein Institute for Organic Chemistry, BRN 1274114, XP002284519.

Database Beilstein Online!, Beilstein Institute for Organic Chemistry, Citation No. 575886, BRN 45135, 41670, XP002284520.

Database Beilstein Online!, Beilstein Institute for Organic Chemistry, BRN 1629436, XP002284521.

Database Beilstein Online!, Beilstein Institute for Organic Chemistry, BRN 1355280, XP002284522.

Database Beilstein Online!, Beilstein Institute for Organic Chemistry, BRN 41863, XP002284523.

Database Beilstein Online!, Beilstein Institute for Organic Chemistry, BRN 39425, XP002284524.

Database Beilstein Online!, Beilstein Institute for Organic Chemistry, BRN 1272804, XP002284525.

Database Beilstein Online!, Beilstein Institute for Organic Chemistry, BRN 4723631, XP002284526.

Database Beilstein Online!, Beilstein Institute for Organic Chemistry, BRN 6282221, XP002284527.

Database Beilstein Online!, Beilstein Institute for Organic Chemistry, BRN 6781196, XP002284528.

Database Beilstein Online!, Beilstein Institute for Organic Chemistry, BRN 7545061, XP002284529.

Database Beilstein Online!, Beilstein Institute for Organic Chemistry, BRN 7950623, XP002284530.

Database Beilstein Online!, Beilstein Institute for Organic Chemistry, BRN 7954188, XP002284531.

Database Beilstein Online!, Beilstein Institute for Organic Chemistry, BRN 2017533, XP002284532.

Database Beilstein Online!, Beilstein Institute for Organic Chemistry, BRN 2024248, XP002284533.

Database Beilstein Online!, Beilstein Institute for Organic Chemistry, BRN 2033596, XP002284534.

Database Beilstein Online!, Beilstein Institute for Organic Chemistry, BRN 2064766, XP002284535.

Database Beilstein Online!, Beilstein Institute for Organic Chemistry, BRN 2065735, XP002284536.

Database Beilstein Online!, Beilstein Institute for Organic Chemistry, BRN 8881860, XP002284537.

Djerassi et al., "Mass Spectrometry in Structural and Stereochemical Problems. LXV. Synthesis and Fragmentation Behaviour of 15-Keto steroids", Journal of the American Chemical Society, 87(4):817-826 (1965).

Gao et al., "A Novel Method for the Synthesis of a C/D-Ring Synthon of Vitamin D Derivatives From Hyodeoxycholic Acid", Tetrahedron Letters, 40(1):131-132 (1999).

Kasal, "Epalons: 6-Substituted Derivatives of 7-Norepiallopregnanolone", Tetrahedron, 56(22):3559-3565 (2000).

Lardy et al., "Ergosteroids II: Biologically Active Metabolites and Synthetic Derivatives of Dehydroepiandrosterone", Steroids: Structure, Function and Regulation, 63(3):158-165 (1998).

Liebermann et al., "D5-Cholestene-3b, 4b, 7a-triol and the Inhibition of the Oxidation of Hydroxyl Groups by Vicinal Substituents", Journal of the American Chemical Society, 72:5211-5218 (1950).

McMorris et al., "Structures of Oogoniol-1, -2, and —3, Steroidal Sex Hormones of the Water Mold", Journal of the American Chemical Society, 97(9):2544-2545 (1975).

Miller et al., "A Ruthenium Catalyzed Osxidation of Steroidal Alkenes to Enones", Tetrahedron Letters, 37(20):3429-3432 (1996).

Nace et al., "Novel Products from the Oxidation of d5 Steroids with Potassium Permanganate in Pyridine", Journal of Organic Chemistry, 35:3846-3851 (1970).

Teng et al., "Sterol Metabolism. XX. Cholesterol 7b-Hydroperoxide", Journal of Organic Chemistry, 38:119-123 (1973).

Witiak et al., "Inhibitors and Stimulators of Cholesterolgenesis Enzymes", Journal of Medicinal Chemistry, 14(8):684-693 (1971).

Bleau G. et al., "Cholesterol Sulfate, Occurrence and possible biological function as an amphipathic lipid in the membrane of the human erythrocyte", Biochim. Ciophys. Acta, vol. 352, No. 1, pp. 1-9, Database HPCAPLUS, AN 1974:461503 (Jan. 1974).

Susan Budavari EDITOR, The Merck Index, An Encyclopedia of Chemicals, Drugs, and Biologicals, 11th Edition, published by Merck & Co., Inc., pp. 396, 574, 1225-1226 (1989).

Edwards et al., "BAREing it all: the adoption of LXR and FXR and their roles in lipid homeostasis", J. Lipid Res., vol. 43, pp. 2-12 (2002).

Hofmann, "The Continuing Importance of Bile Acids in Liver and Intestinal Disease", Arch. Intern. Med., vol. 159, pp. 2647-1658 (1999).

Makishima et al., "Identification of a Nuclear Receptor for Bile Acids", Science, vol. 284, pp. 362-365 (1999).

Roda et al., "New 6-substituted bile acids: physico-chemical and biological properties of 6α-methyl ursodeoxycholic acid and 6α-methyl-7-epicholic acid", J. Lipid Res., vol. 35, pp. 2268-2279 (1994).

Roda et al., "Structure-Activity Relationship Studies on Natural and Synthetic Bile Acid Analogs", Dig. Dis. and Sci., vol. 34, No. 12, pp. 24S-35S (1989).

Runong Wang et al., "Chemical Product Manual", the third version, Pharmaceuticals, Chemical Industry Publishing House, pp. 740 (Jan. 1999).

Clinton et al., "D-Homosteroids. I. Derivatives of D-Homoetiocholan-3βa-ol-11, 17a-dione", Journal of the American Chemical Society, 79:6475-6480 (1957).

Database Beilstein, Beilstein Institute for Organic Chemistry, Frankfurt-Main, DE; BRN 2606100, XP002295651 (Abstract).

DeMarcano et al., "D-Homoandrostanes.2.Preparation and Properties of some Dioxygenated D-Homo-5a-Androstanes", Journal of Organic Chemistry, 42(7):1221-1225 (1977).

DeMarcano et al., "D-Homoandrostanes.4.The Incubation of some D-Homo-5a-Androstanes with Rhizopus Nigricans", *Steroids*, 41(1):1-13 (1983).

Eadon et al., "Synthesis and Biological Activity of D-Bishomo Steroids", *Journal of Medicinal Chemistry*, 15(1):89-91 (1972).

Gao et al., "A Novel Method for the Synthesis of a C/D-Ring Synthon of Vitamin D Derivatives From Hyodeoxycholic Acid", *Tetrahedron Letters*, 40(1):131-132 (1999).

Girdhar et al., "Highly Efficient Lewis Acid Catalyzed, One Step Conversions of 16alpha, 17alpha-epoxy-3beta-hydroxypregn-5-en-20-one to d-homosteroid and DELTA<13>-Steriods", *Tetrahedron*, 57(33):7199-7204 (2001).

Seto et al., "Synthesis and Biological Activity of 6a-Carbabrassinolide: B-Ring Homologation of 6-Oxo-Steroid to 6-Oxo-7a-Homosteroid with Trimethylsilyldiazomethane-Boron Trifluoride Etherate", *Tetrahedron Letters*, 40(12):2359-2362 (1999).

Song et al., "Auto-Oxidized Cholesterol Sulfates are Antagonistic Ligands of Liver X Receptors: Implications for the Developement and Treatment of Atherosclerosis", *Steroids*, 66:409-422 (2001).

English language translation of Kuritzkes et al., "3-epi-Uzarigenin and 3-epa-17α-Uzarigenin", Helvetica Chimica Acta, 14:1502-1515 (1959).

English language translation of Ockels et al., "Dartstellung Von Spezifisch Deuterium-Markierten Analogen Des Androst-5-En-3Beta-Ol", 3Beta-O1, 3Beta-O1, *Tetrahedron*, 32(1):135-142 (1976).

English language translation of Polonia et al., "Die Konstitution des Xysmalogenins", *Helvetica Chimica Acta*, 11:1437-1446 (1959).

English language translation of Tamm et al., "Umwandlung von Cardenoliden durch Mikroorganismen. III Umsetzung von Aglykonen und Glykosiden mit Fusarium lini", *Helvetica Chimica Acta*, 21:239-259 (1959).

English language translation of Tschesche et al., "Uber pflanzliche Herzgifte, XIX. Mitteil,.Die Glykoside der Uzara-Wurzel", *Chemische Berichte*, 85th vol., No. 11:1042-1053 (1952).

Huang et al., "Synthesis of Cholesterol and Its Analog with Fluorinated Side-Chains", *Journal of Fluorine Chemistry*, 43:305-318 (1988).

Kihira et al., "Synthesis of Sulfonate Analogs of Bile Acids", *Steroids*, 57:193-198 (1992).

McKee et al., "HIV-Inhibitory Natural Products. 11. Comparative Studies of Sulfated Sterols from Marine Invertabrates", *J. Med. Chem.*, 37:793-797 (1994).

Riccio et al., "Unusual Sulfated Marine Steroids from the Ophiuroid *Ophioderma Longicaudum*", *Tetrahedron*, 41(24):6041-6046 (1985).

* cited by examiner

METHOD OF TREATING DISORDER RELATED TO HIGH CHOLESTEROL CONCENTRATION

CROSS-REFERENCE TO RELATED APPLICATIONS

The present application claims priority to U.S. Provisional Application Ser. No. 60/348,019 filed Nov. 8, 2001; the present application claims priority to U.S. application Ser. No. 10/137,695 filed May 2, 2002 which claims priority to U.S. Provisional Application Ser. No. 60/288,643 filed May 3, 2001.

FUNDING

Work described herein was supported by grants from the National Institute of Health (AT-00850 and CA-58073). The U.S. government has certain rights in the invention.

TECHNICAL FIELD

The present invention relates to a pharmaceutical compositions comprising a liver X receptor agonist, to methods of treatment comprising administering such a pharmaceutical composition to a subject in need thereof, a method for the manufacture of such a composition, to the use of such a composition in treating disease, to combinations with such a composition with other therapeutic agents, and to kits containing such a composition.

BACKGROUND OF THE INVENTION

It has been well known that a high cholesterol concentration is related to vascular disorders such as coronary heart disease or atherosclerosis. See, e.g., *Essays of an Information Scientist*, 1986, 9, 282–292; and "Cholesterol", Microsoft® Encarta® Encyclopedia 2000. It has also been found that some neurodegenerative diseases such as elevated senile cognitive impairment or dementia (e.g., Alzheimer's disease) can be attributed to an elevated concentration of cholesterol. See, e.g., Sparks, D. L. et al., *Microsc. Res. Tech.*, 2000, 50, 287–290.

The cholesterol concentration can be down-regulated by liver X receptors (LXRs) such as liver X receptor alpha and liver X receptor beta (also called UR). Liver X receptors regulate the cholesterol efflux through the coordinate regulation of genes, e.g., apolipoprotein E (apoE) and ATP-binding cassette transporter A1 (ABCA1), which are involved in lipid metabolism. See, e.g., Laffitte, B. A. et al., *Proc. Natl. Acad. Sci. USA*, 2001, 98 (2), 507–512; Cole, G. M. et al., *Microsc. Res. Tech.*, 2000, 50, 316–324; and Oram J. F et al., *Journal of Lipid Research*, 2001, 42, 1173–1179. Thus, liver X receptor ligands are potential drug candidates for treating a disorder related to a high cholesterol concentration.

SUMMARY OF THE INVENTION

The present invention is directed to methods, kits, combinations, and compositions for treating, preventing or reducing the risk of developing a disorder or disease related to, or the symptoms associated with, high blood serum concentrations of cholesterol in a subject.

One aspect of this invention relates to a method of treating a disorder related to high cholesterol concentration, comprising administering to a subject in need thereof a compound of formula (I):

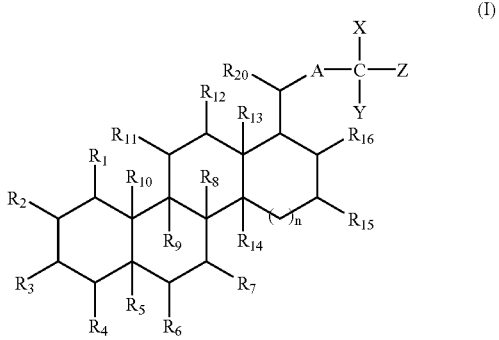

In formula (I), each of $R_1$, $R_2$, $R_3$, $R_4$, $R_5$, $R_6$, $R_7$, $R_{11}$, $R_{12}$, $R_{15}$, $R_{16}$, and $R_{20}$, independently, is hydrogen, halo, alkyl, haloalkyl, hydroxy, amino, carboxyl, oxo, sulfonic acid, or alkyl that is optionally inserted with —NH—, —N(alkyl)-, —O—, —S—, —SO—, —SO$_2$—, —O—SO$_2$—, —SO$_2$—O—, —SO$_3$—O—, —CO—, —CO—O—, —O—CO—, —CO—NR'—, or —NR'—CO—; each of $R_8$, $R_9$, $R_{10}$, $R_{13}$, and $R_{14}$, independently, is hydrogen, halo, alkyl, haloalkyl, hydroxyalkyl, alkoxy, hydroxy, or amino; n is 0, 1, or 2; A is alkylene, alkenylene, or alkynylene; and each of X, Y, and Z, independently, is alkyl, haloalkyl, —OR', —SR', —NR'R", —N(OR')R", or—N(SR')R"; or X and Y together are =O, =S, or =NR'; wherein each of R' and R", independently, is hydrogen, alkyl, or haloalkyl. Note that the carbon atoms shown in formula (I) are saturated with hydrogen unless otherwise indicated.

Each of the term "alkyl," the prefix "alk" (as in alkoxy), and the suffix "-alkyl" (as in hydroxyalkyl) refers to a $C_{1-8}$ hydrocarbon chain, linear (e.g., butyl) or branched (e.g., iso-butyl). Alkylene, alkenylene, and alkynylene refer to divalent $C_{1-8}$ alkyl (e.g., ethylene), alkene, and alkyne radicals, respectively. Unless otherwise defined, all technical and scientific terms used herein have the same meaning as commonly understood by one of ordinary skills in the art to which this invention belongs.

Referring to formula (I), subsets of the compounds that can be used to practice the method of this invention include those wherein each of $R_1$, $R_2$, $R_4$, $R_7$, $R_8$, $R_9$, $R_{11}$, $R_{12}$, $R_{14}$, $R_{15}$, $R_{16}$, independently, is hydrogen; each of $R_{10}$, $R_{13}$, and $R_{20}$, independently, is an alkyl (e.g., methyl, ethyl, butyl, or iso-butyl); n is 0; and A is alkylene; those wherein $R_5$ is hydrogen (e.g., β hydrogen), and each of $R_3$ and $R_6$, independently, is hydroxy (e.g., α hydroxy); those wherein each of X, Y, and Z, independently, is alkyl (e.g., methyl, propyl, or hexyl), haloalkyl (e.g., trifluoromethyl, or 3-chloropropyl), —OR' (e.g., hydroxy or methyocy), or —SR'; and those wherein X and Y together are =O or =S; and Z is —OR', —SR', —NR'R" (e.g., ethylmethylamino), —N(OR')R" (e.g., methoxymethylamino), or —N(SR')R".

Shown below are hypocholamide (with carbon atoms numbered) and hypocholaride, two of the compounds described above that can be used to practice the method of this invention:

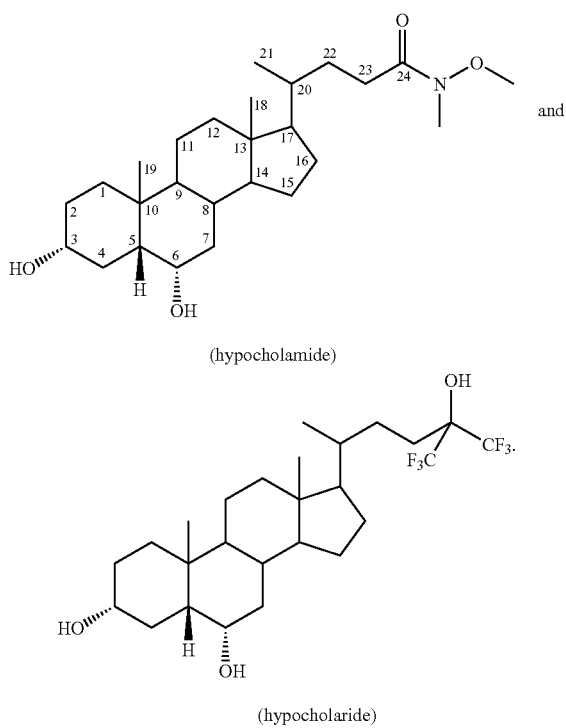

(hypocholamide)

(hypocholaride)

A compound of the present invention also includes a pharmaceutically-acceptable salt, an ester, an amide, an enantiomer, an isomer, a tautomer, a polymorph, a prodrug, or a derivative thereof. Such salts, for example, can be formed between a positively charged substituent in a compound (e.g., amino) and an anion. Suitable anions include, but are not limited to, chloride, bromide, iodide, sulfate, nitrate, phosphate, citrate, methanesulfonate, trifluoroacetate, and acetate. Likewise, a negatively charged substituent in a compound (e.g., carboxylate) can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing compounds described above.

The details of one or more embodiments of the invention are set forth in the accompanying description below. Other features, objects, and advantages of the invention will be apparent from the description and claims.

DETAILED DESCRIPTION OF THE INVENTION

The present invention is directed to a method of treating a condition or disorder where treatment with a liver X receptor alpha agonist is indicated, the method comprises administration of a composition of the present invention to a subject in need thereof.

Another aspect of this invention relates to a pharmaceutical composition for treating a disorder related to a high cholesterol concentration in blood serum of a subject. This composition includes an effective amount of a compound of formula (I) and a pharmaceutically acceptable carrier. Also within the scope of this invention is the use of a compound of formula (I) for the manufacture of a medicament to be used in treating one of such disorders. Treatment of these conditions is accomplished by administering to a subject a therapeutically effective amount of a compound or composition of the present invention.

In one embodiment of the present invention, the disorder that can be treated by the methods, kits, combinations, and compositions of this invention is a vascular disorder or a neurodegenerative disorder, for example, arteriosclerosis, senile cognitive impairment, and/or dementia (e.g., Alzheimer's disease).

Compounds that can be used to practice the methods, kits, combinations, and compositions of the present invention can be synthesized according to methods well known in the art by using a suitable steroid as a starting material. Illustratively, such a steroid possesses a substituent at C-20 (the carbon to which $R_{20}$ is attached, see formula (I) or the structure of hypocholamide shown above) that can be modified to contain a moiety defined by X, Y, and Z (also shown in formula (I)). Examples of the steroid include cholic acid, dehydrocholic acid, deoxycholic acid, lithocholic acid, ursodeoxycholic acid, hyocholic acid, hyodeoxycholic acid, and cholanoic acid. They are either commercially available or can be synthesized according to a method described in the literature, e.g., Roda et al., *F. Lipid Res.*, 1994, 35: 2268–2279; or Roda et al., *Dig. Dis. Sci.*, 1987, 34: 24S-35S.

A compound that has an amide-containing substituent at C-20 (i.e., X and Y together are =O, and Z is amine) can be prepared by reacting a steroid having a carboxyl-containing substituent at C-20 with an amino-containing compound (such as dimethylamine, aniline, glycine, and phenylalanine). Similarly, a compound that has an ester-containing substitutent at C-20 (i.e., X and Y together are =O, and Z is alkoxy) can be prepared by reacting a steroid having a carboxyl-containing substituent at C-20 with a hydroxyl-containing compound (such as ethanol and isopropanol). The amide- or ester-forming reaction can take place in any suitable solvents. If the reaction takes place in an aqueous solution, isolation of the steroid product for in vitro or in vivo screening assays may not be necessary.

A compound that has a carbonyl-containing substituent at C-20 (i.e., X and Y together are =O) can be converted, e.g., to a thiocarbonyl-containing compound (i.e., X and Y together are =S) by reacting it with sulfur hydride, or to an imino-containing compound (i.e., X and Y together are =NR) by reacting it with hydrazine. See, e.g., Janssen et al. (Ed.), *Organosulfur Chemistry*, Wiley: New York, 1967, 219–240; and Patai et al. (Ed.), *The Chemistry of the Carbon-Nitrogen Double Bond*, Wiley: New York, 1970, 64–83 and 465–504.

Substituents at positions other than C-20, if necessary, can further be introduced by methods well known in the art. For instance, a hydroxyl substituent at C-3 can be converted to an ester substituent by reacting it with an acid such as acetic acid.

Due to the simplicity of the reaction, it can be easily automated. Isolation and quantification of the product can be done by thin-layer chromatography, high pressure liquid chromatography, gas chromatography, capillary electrophoresis, or other analytical and preparative procedures.

A compound that does not contain a carbonyl, thiocarbonyl, or imino group in the C-20 substituent can also be prepared by methods well known in the art. For instance, 3α,6α,24-trihydroxy-5β-24,24-di(trifluoromethyl)-cholane (i.e., hypocholaride) can be prepared according to the following scheme:

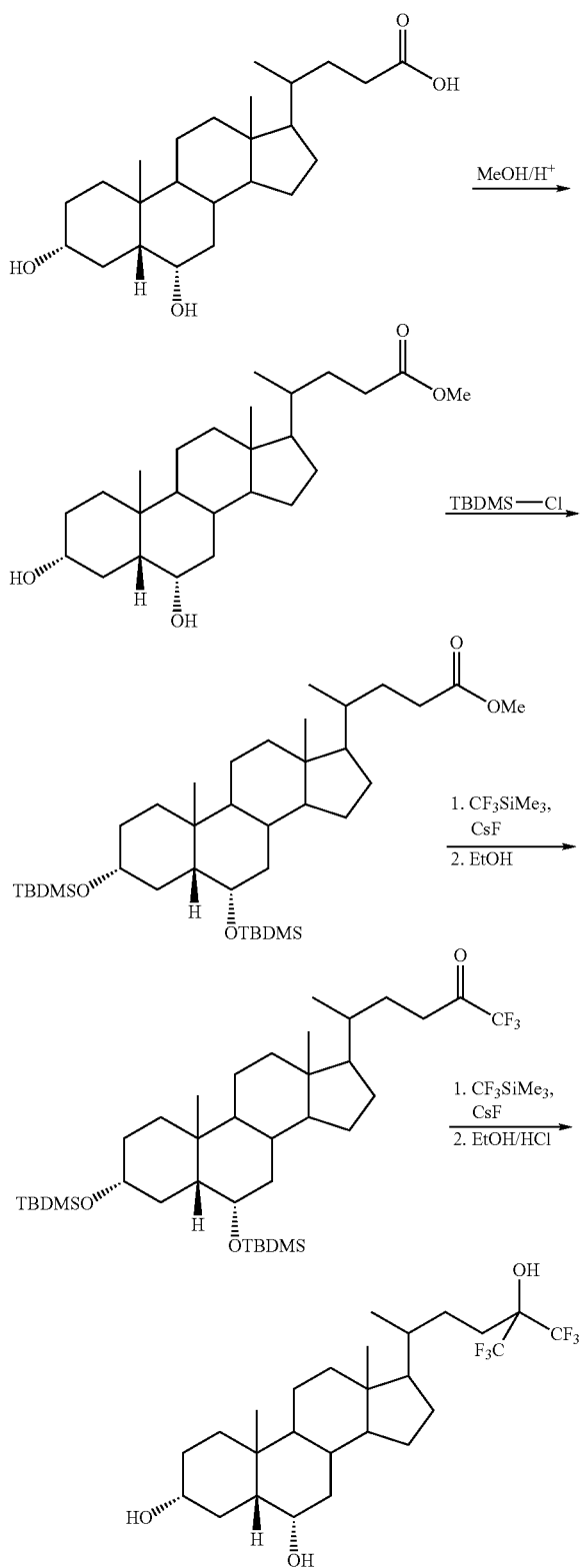

As shown in the above scheme, 3α,6α-dihydroxy-5β-24-cholanoic acid is first reacted with methanol in the presence of an acid to afford its methyl ester. The ester is subsequently treated for protection of the 3α and 6α hydroxyl groups, and then converted to a ketone. The ketone is subsequently converted to an alcohol, α-substituted with trifluoromethyl. Finally, the alcohol is deprotected to afford hypocholaride.

In another embodiment, the compounds of the present invention have an overall hypolipidemic effect in a hypercholesterolemic subject. While not wishing to be bound by any particular theory, it is believed that the compounds of formula I exhibit a unique pharmacokinetic profile, for example, in one embodiment, the compounds of formula I do not substantially increase the serum triglyceride level in a subject, while at the same time lowering serum LDL cholesterol levels; therefore, the compounds of the present invention represent a novel class of therapeutic agents for cholesterol management.

In one embodiment of the present invention, the compounds activate the liver X receptor alpha (that is, an liver X receptor alpha agonist). In another embodiment of the present invention, the compounds selectively activate the liver X receptor alpha (that is, a selective liver X receptor alpha agonist) relative to liver X receptor beta. In one embodiment, the compounds of the present invention have a selectivity ratio of liver X receptor alpha relative to liver X receptor beta of at least 2; in another embodiment have a selectivity ratio of at least 25; in another embodiment have a selectivity ratio of at least 50; in another embodiment have a selectivity ratio of at least 100, and in another embodiment have a selectivity ratio of at least 1,000. As used herein, the term liver X receptor agonist encompasses both a liver X receptor alpha agonist and a selective liver X receptor alpha agonist, unless the context in which it is used dictates otherwise.

Illustratively, agonists of liver X receptor alpha used in the treatment, prevention or reduction in the risk of developing a vascular disorder or a neurodegenerative disorder may activate the liver X receptor alpha activity through a variety of mechanisms. By way of example, the liver X receptor alpha agonist used in the methods described herein may activate the receptor directly by binding to the receptor, such as a ligand. While not wishing to be bound by theory, the use of a liver X receptor alpha selective activator can be advantageous in that they may increase the HDL cholesterol level, and/or decrease the LDL cholesterol level in serum or in the liver without increasing serum triglycerides levels.

An in vitro assay can be conducted to preliminarily screen a compound thus obtained for its efficacy in agonizing liver X receptors and increasing the amount of apoE, thereby decreasing the cholesterol level and treating a disorder related to a high cholesterol concentration. For instance, kidney cells are transfected with a luciferase reporter gene (which includes a human c-fos minimal promoter) and liver X receptor. After incubating the transfected cells with a compound to be tested, the activity of luciferase is measured to determine the transactivation extent of the reporter gene.

Compounds that show efficacy in the preliminary in vitro assay can be further evaluated in an animal study by a method also well known in the art. For example, a compound can be orally administered to mice. The efficacy of the compound can be determined by comparing cholesterol levels in various tissues of the treated mice with those in non-treated mice. Song et al., *Steroids* 2001, 66, 673–681.

The term "treat" or "treatment" as used herein refers to any treatment of a disorder or disease associated with a disease or disorder related to high blood serum concentration of cholesterol in a subject, and includes, but is not limited to, preventing the disorder or disease from occurring in a subject which may be predisposed to the disorder or disease, but has not yet been diagnosed as having the disorder or disease; inhibiting the disorder or disease, for example, arresting the development of the disorder or disease; relieving the disorder or disease, for example, causing regression of the disorder or disease; or relieving the condition caused by the disease or disorder, for example, stopping the symptoms of the disease or disorder.

The term "prevent" or "prevention," in relation to a disease or disorder related to high blood serum concentration of cholesterol in a subject, means no disease or disorder development if none had occurred, or no further disorder or disease development if there had already been development of the disorder or disease.

The phrase "high blood serum concentration of cholesterol" or "high blood serum cholesterol concentration" as used herein refers to cholesterol blood serum levels in a subject that is generally above that which has generally been determined healthy or normal, and is, or can lead to the development of a disease or disorder associated with high serum concentrations of cholesterol. The healthy or normal level will vary from species to species and even subject to subject, or be age specific, for example, however, a person of ordinary skill in the art will be able to determine a healthy or normal level for each subject. Healthy or normal levels of cholesterol can be calculated by referencing many scientific and medical publications. Generally, cholesterol is measured in a subject as total plasma cholesterol, LDL cholesterol and HDL cholesterol. Illustratively, in an adult human, high blood serum cholesterol concentration is generally considered to be above about 5.2 mmol/L (200 mg/dL) for total plasma cholesterol; and/or above about 3.36 mmol/L (130 mg/dL) for LDL cholesterol. In another embodiment, in an adult human, high blood serum cholesterol concentration is generally considered to be above about 5.2 to about 6.18 mmol/L (200–239 mg/dL) for total plasma cholesterol; and/or above about 3.36 to about 4.11 mmol/L (130–159 mg/dL) for LDL cholesterol. In yet another embodiment, in an adult human, high blood serum cholesterol concentration is generally considered to be above about 6.21 mmol/L (240 mg/dL) for total plasma cholesterol; and/or above about 4.14 mmol/L (160 mg/dL) for LDL cholesterol level is.

An effective amount of an efficacious compound can be formulated with a pharmaceutically acceptable carrier to form a pharmaceutical composition before being administered for treatment of a disease related to a high cholesterol concentration. "An effective amount" or "pharmacologically effective amount" refers to the amount of the compound which is required to confer therapeutic effect on the treated subject. The interrelationship of dosages for animals and humans (based on milligrams per square meter of body surface) is described by Freireich et al., *Cancer Chemother. Rep.* 1966, 50, 219. Body surface area may be approximately determined from height and weight of the patient. See, e.g., Scientific Tables, Geigy Pharmaceuticals, Ardley, New York, 1970, 537. Effective doses will also vary, as recognized by those skilled in the art, depending on the route of administration, the excipient usage, and the optional co-usage with other therapeutic treatments.

Toxicity and therapeutic efficacy of the active ingredients can be determined by standard pharmaceutical procedures, e.g., for determining LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Included in the methods, kits, combinations and pharmaceutical compositions of the present invention are the isomeric forms and tautomers of the described compounds and the pharmaceutically-acceptable salts thereof. Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, b-hydroxybutyric, galactaric and galacturonic acids.

The term "prodrug" refers to a drug or compound in which the pharmacological action (active curative agent) results from conversion by metabolic processes within the body. Prodrugs are generally considered drug precursors that, following administration to a subject and subsequent absorption, are converted to an active or a more active species via some process, such as a metabolic process. Other products from the conversion process are easily disposed of by the body. Prodrugs generally have a chemical group present on the prodrug which renders it less active and/or confers solubility or some other property to the drug. Once the chemical group has been cleaved from the prodrug the more active drug is generated. Prodrugs may be designed as reversible drug derivatives and utilized as modifiers to enhance drug transport to site-specific tissues. The design of prodrugs to date has been to increase the effective water solubility of the therapeutic compound for targeting to regions where water is the principal solvent. For example, Fedorak, et al., Am. J. Physiol, 269:G210–218 (1995), describe dexamethasone-beta-D-glucuronide. McLoed, et al., Gastroenterol., 106:405–413 (1994), describe dexamethasone-succinate-dextrans. Hochhaus, et al., Biomed. Chrom., 6:283–286 (1992), describe dexamethasone-21-sulphobenzoate sodium and dexamethasone-21-isonicotinate. Additionally, J. Larsen and H. Bundgaard [Int. J. Pharmaceutics, 37, 87 (1987)] describe the evaluation of N-acylsulfonamides as potential prodrug derivatives. J. Larsen et al., [Int. J. Pharmaceutics, 47, 103 (1988)] describe the evaluation of N-methylsulfonamides as potential prodrug derivatives. Prodrugs are also described in, for example, Sinkula et al., J. Pharm. Sci., 64:181–210 (1975).

The term "derivative" refers to a compound that is produced from another compound of similar structure by the replacement of substitution of one atom, molecule or group by another. For example, a hydrogen atom of a compound may be substituted by alkyl, acyl, amino, etc., to produce a derivative of that compound.

"Plasma concentration" refers to the concentration of a substance in blood plasma or blood serum.

"Drug absorption" or "absorption" refers to the process of movement from the site of administration of a drug toward the systemic circulation, for example, into the bloodstream of a subject.

"Bioavailability" refers to the extent to which an active moiety (drug or metabolite) is absorbed into the general circulation and becomes available at the site of drug action in the body.

"Metabolism" refers to the process of chemical alteration of drugs in the body.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Half-life" refers to the time required for the plasma drug concentration or the amount in the body to decrease by 50% from its maximum concentration.

The use of the term "about" in the present disclosure means "approximately," and illustratively, the use of the term "about" indicates that dosages outside the cited ranges may also be effective and safe, and such dosages are also encompassed by the scope of the present claims.

The term "measurable serum concentration" means the serum concentration (typically measured in mg, μg, or ng of therapeutic agent per ml, dl, or l of blood serum) of a therapeutic agent absorbed into the bloodstream after administration.

The term "pharmaceutically acceptable" is used adjectivally herein to mean that the modified noun is appropriate for use in a pharmaceutical product. Pharmaceutically acceptable cations include metallic ions and organic ions. More preferred metallic ions include, but are not limited to appropriate alkali metal (Group Ia) salts, alkaline earth metal (Group IIa) salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

The compositions of the present invention are usually administered in the form of pharmaceutical compositions. These compositions can be administered by any appropriate route including, but not limited to, oral, rectal, transdermal, parenteral (for example, subcutaneous, intramuscular, intravenous, intramedullary and intradermal injections, or infusion techniques administration), intranasal (for example, nasogastric tube), transmucosal, implantation, inhalation spray, vaginal, topical, and buccal (for example, sublingual). Such preparations may routinely contain buffering agents, preservatives, penetration enhancers, compatible carriers and other therapeutic ingredients.

The present invention also includes methods employing a pharmaceutical composition that contains the composition of the present invention associated with pharmaceutically acceptable carriers or excipients. As used herein, the terms "pharmaceutically acceptable carrier" or "pharmaceutically acceptable excipients" includes any and all solvents, dispersion media, coatings, antibacterial and antifungal agents, isotonic and absorption delaying agents, and the like. The use of such media and agents for ingestible substances is well known in the art. Except insofar as any conventional media or agent is incompatible with the compositions, its use is contemplated. Supplementary active ingredients can also be incorporated into the compositions.

In making the compositions of the present invention, the compositions(s) can be mixed with a pharmaceutically acceptable excipient, diluted by the excipient or enclosed within such a carrier, which can be in the form of a capsule, sachet, paper or other container. The carrier materials that can be employed in making the composition of the present invention are any of those commonly used excipients in pharmaceutics and should be selected on the basis of compatibility with the active drug and the release profile properties of the desired dosage form. Illustratively, a pharmaceutical excipient except active drugs are chosen below as examples:

(a) Binders such as acacia, alginic acid and salts thereof, cellulose derivatives, methylcellulose, hydroxyethyl cellulose, hydroxypropyl cellulose, magnesium aluminum silicate, polyethylene glycol, gums, polysaccharide acids, bentonites, hydroxypropyl methylcellulose, gelatin, polyvinylpyrrolidone, polyvinylpyrrolidone/vinyl acetate copolymer, crospovidone, povidone, polymethacrylates, hydroxypropylmethylcellulose, hydroxypropylcellulose, starch, pregelatinized starch, ethylcellulose, tragacanth, dextrin, microcrystalline cellulose, sucrose, or glucose, and the like.

(b) Disintegration agents such as starches, pregelatinized corn starch, pregelatinized starch, celluloses, cross-linked carboxymethylcellulose, sodium starch glycolate, crospovidone, cross-linked polyvinylpyrrolidone, croscarmellose sodium, a calcium, a sodium alginate complex, clays, alginates, gums, or sodium starch glycolate, and any disintegration agents used in tablet preparations.

(c) Filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

(d) Surfactants such as sodium lauryl sulfate, sorbitan monooleate, polyoxyethylene sorbitan monooleate, polysorbates, polaxomers, bile salts, glyceryl monostearate, Pluronic™ line (BASF), and the like.

(e) Solubilizer such as citric acid, succinic acid, fumaric acid, malic acid, tartaric acid, maleic acid, glutaric acid sodium bicarbonate and sodium carbonate and the like.

(f) Stabilizers such as any antioxidation agents, buffers, or acids, and the like, can also be utilized.

(g) Lubricants such as magnesium stearate, calcium hydroxide, talc, sodium stearyl fumarate, hydrogenated vegetable oil, stearic acid, glyceryl behapate, magnesium, calcium and sodium stearates, stearic acid, talc, waxes, Stearowet, boric acid, sodium benzoate, sodium acetate, sodium chloride, DL-leucine, polyethylene glycols, sodium oleate, or sodium lauryl sulfate, and the like.

(h) Wetting agents such as oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, or sodium lauryl sulfate, and the like.

(i) Diluents such lactose, starch, mannitol, sorbitol, dextrose, microcrystalline cellulose, dibasic calcium phosphate, sucrose-based diluents, confectioner's sugar, monobasic calcium sulfate monohydrate, calcium sulfate dihydrate, calcium lactate trihydrate, dextrates, inositol, hydrolyzed cereal solids, amylose, powdered cellulose, calcium carbonate, glycine, or bentonite, and the like.

(j) Anti-adherents or glidants such as talc, corn starch, DL-leucine, sodium lauryl sulfate, and magnesium, calcium, or sodium stearates, and the like.

(k) Pharmaceutically compatible carrier comprises acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, or pregelatinized starch, and the like.

Additionally, drug formulations are discussed in, for example, Hoover, John E., *Remington's The Science and Practice of Pharmacy* (2000). Another discussion of drug formulations can be found in Liberman, H. A. and Lachman, L., Eds., *Pharmaceutical Dosage Forms*, Marcel Decker, New York, N.Y., 1980.

Besides being useful for human treatment, the present invention is also useful for other subjects including veterinary animals, reptiles, birds, exotic animals and farm animals, including mammals, rodents, and the like. Mammal includes a primate, for example, a monkey, or a lemur, a horse, a dog, a pig, or a cat. A rodent includes a rat, a mouse, a squirrel, or a guinea pig.

The pharmaceutical compositions of the present invention are useful where administration of a liver X receptor alpha agonist is indicated. It has been found that these compositions are particularly effective in the treatment of a vascular disorder or a neurodegenerative disorder, such as arteriosclerosis, high cholesterol serum concentration, senile cognitive impairment and/or dementia (for example, Alzheimer's disease).

For treatment of a disorder related to a vascular disorder or a neurodegenerative disorder, compositions of the invention can be used to provide a dose of a compound of the present invention of about 5 ng to about 1000 mg, or about 100 ng to about 600 mg, or about 1 mg to about 500 mg, or about 20 mg to about 400 mg. A dose can be administered in one to about four doses per day, or in as many doses per day to elicit a therapeutic effect. Illustratively, a dosage unit of a composition of the present invention can typically contain, for example, about 5 ng, 50 ng 100 ng, 500 ng, 1 mg, 10 mg, 20 mg, 40 mg, 80 mg, 100 mg, 125 mg, 150 mg, 200 mg, 250 mg, 300 mg, 350 mg, 400 mg, 450 mg, 500 mg, 550 mg, 600 mg, 700 mg, 800 mg, 900 mg, or 1000 mg of a compound of the present invention. The dosage form can be selected to accommodate the desired frequency of administration used to achieve the specified dosage. The amount of the unit dosage form of the composition that is administered and the dosage regimen for treating the condition or disorder depends on a variety of factors, including, the age, weight, sex and medical condition, of the subject, the severity of the condition or disorder, the route and frequency of administration, and this can vary widely, as is well known.

In one embodiment of the present invention, the composition is administered to a subject in an effective amount, that is, the composition is administered in an amount that achieves a therapeutically-effective dose of a compound of the present invention in the blood serum of a subject for a period of time to elicit a desired therapeutic effect. Illustratively, in a fasting adult human (fasting for generally at least 10 hours) the composition is administered to achieve a therapeutically-effective dose of a compound of the present invention in the blood serum of a subject from about 5 minutes after administration of the composition. In another embodiment of the present invention, a therapeutically-effective dose of the compound of the present invention is achieved in the blood serum of a subject at about 10 minutes from the time of administration of the composition to the subject. In another embodiment of the present invention, a therapeutically-effective dose of the compound of the present invention is achieved in the blood serum of a subject at about 20 minutes from the time of administration of the composition to the subject. In yet another embodiment of the present invention, a therapeutically-effective dose of the compound of the present invention is achieved in the blood serum of a subject at about 30 minutes from the time of administration of the composition to the subject. In still another embodiment of the present invention, a therapeutically-effective dose of the compound of the present invention is achieved in the blood serum of a subject at about 40 minutes from the time of administration of the composition to the subject. In one embodiment of the present invention, a therapeutically-effective dose of the compound of the present invention is achieved in the blood serum of a subject at about 20 minutes to about 12 hours from the time of administration of the composition to the subject. In another embodiment of the present invention, a therapeutically-effective dose of the compound of the present invention is achieved in the blood serum of a subject at about 20 minutes to about 6 hours from the time of administration of the composition to the subject. In yet another embodiment of the present invention, a therapeutically-effective dose of the compound of the present invention is achieved in the blood serum of a subject at about 20 minutes to about 2 hours from the time of administration of the composition to the subject. In still another embodiment of the present invention, a therapeutically-effective dose of the compound of the present invention is achieved in the blood serum of a subject at about 40 minutes to about 2 hours from the time of administration of the composition to the subject. And in yet another embodiment of the present invention, a therapeutically-effective dose of the compound of the present invention is achieved in the blood serum of a subject at about 40 minutes to about 1 hour from the time of administration of the composition to the subject.

In one embodiment of the present invention, a composition of the present invention is administered at a dose suitable to provide a blood serum concentration with a half maximum dose of a compound of the present invention. Illustratively, a blood serum concentration of about 0.01 to about 1000 nM, or about 0.1 to about 750 nM, or about 1 to about 500 nM, or about 20 to about 1000 nM, or about 100 to about 500 nM, or about 200 to about 400 nM is achieved in a subject after administration of a composition of the present invention. Contemplated compositions of the present invention provide a therapeutic effect as compound of the present invention medications over an interval of about 5 minutes to about 24 hours after administration, enabling once-a-day or twice-a-day administration if desired. In one embodiment of the present invention, the composition is administered at a dose suitable to provide an average blood serum concentration with a half maximum dose of a compound of the present invention of at least about 1 µg/ml; or at least about 5 µg/ml, or at least about 10 µg/ml, or at least about 50 µg/ml, or at least about 100 µg/ml, or at least about 500 µg/ml, at least about 1000 µg/ml in a subject about 10, 20, 30, or 40 minutes after administration of the composition to the subject.

The amount of therapeutic agent necessary to elicit a therapeutic effect can be experimentally determined based on, for example, the absorption rate of the agent into the blood serum, the bioavailability of the agent, and the potency for modulating a liver X receptor. It is understood, however, that specific dose levels of the therapeutic agents of the present invention for any particular subject depends upon a variety of factors including the activity of the specific compound employed, the age, body weight, general health, sex, and diet of the subject (including, for example, whether the subject is in a fasting or fed state), the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for subject administration. Studies in animal models generally may be used for guidance regarding effective dosages for treatment of gastrointestinal disorders or diseases in accordance with the present invention. In terms of treatment protocols, it should be appreciated that the dosage to be administered will depend on several factors, including the particular agent that is administered, the route administered, the condition of the particular subject, etc. Generally speaking, one will desire to administer an amount of the compound that is effective to achieve a serum level commensurate with the concentrations found to be effective in vitro for a period of time effective to elicit a therapeutic effect. Thus, where a compound is found to demonstrate in vitro activity at, for example, a half-maximum effective dose of 200 nM, one will desire to administer an amount of the drug that is effective to provide about a half-maximum effective dose of 200 nM concentration in vivo for a period of time that elicits a desired therapeutic effect, for example, agonizing a liver X receptor, treating a disorder related to high cholesterol concentration, treating arteriosclerosis, treating a senile cognitive impairment, treating dementia, treating Alzheimer's, and other indicators as are selected as appropriate measures by those skilled in the art. Determination of these parameters is well within the skill of the art. These considerations are well known in the art and are described in standard textbooks.

In order to measure and determine the effective amount of a compound of the present invention to be delivered to a subject, serum compound of the present invention concentrations can be measured using standard assay techniques.

Contemplated compositions of the present invention provide a therapeutic effect over an interval of about 30 minutes to about 24 hours after administration to a subject. In one embodiment compositions provide such therapeutic effect in about 30 minutes. In another embodiment compositions provide therapeutic effect over about 24 hours, enabling once-a-day administration.

In another aspect, the present invention is directed to therapeutic methods of treating a condition or disorder where treatment with a liver X receptor alpha is indicated, the method comprises the oral administration of one or more compositions of the present invention to a subject in need thereof. In one embodiment, the condition or disorder is a vascular disorder or a neurodegenerative disorder.

The present methods, kits, and compositions can also be used in combination ("combination therapy") with another pharmaceutical agent that is indicated for treating or preventing a vascular disorder or a neurodegenerative disorder, such as, for example, a atatin (e.g., lovastatin) an angiotensin converting enzyme inhibitor, an angiotensin II receptor antagonist, an antiarrhythmic, an anticholersteremic, a diuretic, a dopamine receptor agonist, a dopamine receptor antagonist, or a vasodilator, which are commonly administered to treat, prevent, or minimize the symptoms and complications related to this disorder. These drugs have certain disadvantages associated with their use. Some of these drugs are not completely effective in the treatment of the aforementioned conditions and/or produce adverse side effects, such as mental confusion, constipation, diarrhea, etc. However, when used in conjunction with the present invention, that is, in combination therapy, many if not all of these unwanted side effects can be reduced or eliminated. The reduced side effect profile of these drugs is generally attributed to, for example, the reduce dosage necessary to achieve a therapeutic effect with the administered combination.

The phrase "combination therapy" embraces the administration of a composition of the present invention in conjunction with another pharmaceutical agent that is indicated for treating or preventing a vascular disorder or a neurodegenerative disorder in a subject, as part of a specific treatment regimen intended to provide a beneficial effect from the co-action of these therapeutic agents for the treatment of a vascular disorder or a neurodegenerative disorder. The beneficial effect of the combination includes, but is not limited to, pharmacokinetic or pharmacodynamic co-action resulting from the combination of therapeutic agents. Administration of these therapeutic agents in combination typically is carried out over a defined time period (usually substantially simultaneously, minutes, hours, days, weeks, months or years depending upon the combination selected). "Combination therapy" generally is not intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, where each therapeutic agent is administered at a different time, as well as administration of these therapeutic agents, or at least two of the therapeutic agents, in a substantially simultaneous manner. Substantially simultaneous administration can be accomplished, for example, by administering to the subject a single tablet or capsule having a fixed ratio of each therapeutic agent or in multiple, single capsules, or tablets for each of the therapeutic agents. Sequential or substantially simultaneous administration of each therapeutic agent can be effected by any appropriate route. The composition of the present invention can be administered orally or nasogastric, while the other therapeutic agent of the combination can be administered by any appropriate route for that particular agent, including, but not limited to, an oral route, a percutaneous route, an intravenous route, an intramuscular route, or by direct absorption through mucous membrane tissues. For example, the composition of the present invention is administered orally or nasogastric and the therapeutic agent of the combination may be administered orally, or percutaneously. The sequence in which the therapeutic agents are administered is not narrowly critical. "Combination therapy" also can embrace the administration of the therapeutic agents as described above in further combination with other biologically active ingredients, such as, but not limited to, an analgesic, for example, and with non-drug therapies, such as, but not limited to, surgery.

The therapeutic compounds which make up the combination therapy may be a combined dosage form or in separate dosage forms intended for substantially simultaneous administration. The therapeutic compounds that make up the combination therapy may also be administered sequentially, with either therapeutic compound being administered by a regimen calling for two step administration. Thus, a regimen may call for sequential administration of the therapeutic compounds with spaced-apart administration of the separate, active agents. The time period between the multiple administration steps may range from, for example, a few minutes to several hours to days, depending upon the properties of each therapeutic compound such as potency, solubility, bioavailability, plasma half-life and kinetic profile of the therapeutic compound, as well as depending upon the effect of food ingestion and the age and condition of the subject. Circadian variation of the target molecule concentration may also determine the optimal dose interval. The therapeutic compounds of the combined therapy whether administered simultaneously, substantially simultaneously, or sequentially, may involve a regimen calling for administration of one therapeutic compound by oral route and another therapeutic compound by an oral route, a percutaneous route, an intravenous route, an intramuscular route, or by direct absorption through mucous membrane tissues, for example. Whether the therapeutic compounds of the combined therapy are administered orally, by inhalation spray, rectally, topically, buccally (for example, sublingual), or parenterally (for example, subcutaneous, intramuscular, intravenous and intradermal injections, or infusion techniques), separately or together, each such therapeutic compound will be contained in a suitable pharmaceutical formulation of pharmaceutically-acceptable excipients, diluents or other formulations components.

For oral administration, the pharmaceutical composition can contain a desired amount of a liver X receptor alpha agonist and be in the form of, for example, a tablet, a hard or soft capsule, a lozenge, a cachet, a dispensable powder, granules, a suspension, an elixir, a liquid, or any other form reasonably adapted for oral administration. Illustratively, such a pharmaceutical composition can be made in the form of a discrete dosage unit containing a predetermined amount of the liver X receptor alpha agonist such as a tablet or a capsule. Such oral dosage forms can further comprise, for example, buffering agents. Tablets, pills and the like additionally can be prepared with enteric coatings.

Pharmaceutical compositions suitable for buccal (sublingual) administration include, for example, lozenges comprising a liver X receptor alpha agonist in a flavored base, such as sucrose, and acacia or tragacanth, and pastilles comprising a liver X receptor alpha agonist in an inert base such as gelatin and glycerin or sucrose and acacia.

Liquid dosage forms for oral administration can include pharmaceutically acceptable emulsions, solutions, suspensions, syrups, and elixirs containing inert diluents commonly used in the art, such as water. Such compositions can also comprise, for example, wetting agents, emulsifying and suspending agents, and sweetening, flavoring, and perfuming agents.

Examples of suitable liquid dosage forms include, but are not limited, aqueous solutions comprising a liver X receptor alpha agonist and beta-cyclodextrin or a water soluble derivative of beta-cyclodextrin such as sulfobutyl ether beta-cyclodextrin; heptakis-2,6-di-O-methyl-beta-cyclodextrin; hydroxypropyl-beta-cyclodextrin; and dimethyl-beta-cyclodextrin.

The pharmaceutical compositions of the present invention can also be administered by injection (intravenous, intramuscular, subcutaneous). Such injectable compositions can employ, for example, saline, dextrose, or water as a suitable carrier material. The pH value of the composition can be adjusted, if necessary, with suitable acid, base, or buffer. Suitable bulking, dispersing, wetting or suspending agents, including mannitol and polyethylene glycol (such as PEG 400), can also be included in the composition. A suitable parenteral composition can also include a liver X receptor alpha agonist in injection vials. Aqueous solutions can be added to dissolve the composition prior to injection.

The pharmaceutical compositions can be administered in the form of a suppository or the like. Such rectal formulations preferably contain a liver X receptor alpha agonist in a total amount of, for example, about 0.075 to about 75% w/w, or about 0.2 to about 40% w/w, or about 0.4 to about 15% w/w. Carrier materials such as cocoa butter, theobroma oil, and other oil and polyethylene glycol suppository bases can be used in such compositions. Other carrier materials such as coatings (for example, hydroxypropyl methylcellulose film coating) and disintegrants (for example, croscarmellose sodium and cross-linked povidone) can also be employed if desired.

These pharmaceutical compositions can be prepared by any suitable method of pharmacy which includes the step of bringing into association a liver X receptor alpha agonist of the present invention and a carrier material or carriers materials. In general, the compositions are uniformly and intimately admixing the active compound with a liquid or finely divided solid carrier, or both, and then, if necessary, shaping the product. For example, a tablet can be prepared by compressing or molding a powder or granules of the compound, optionally with one or more accessory ingredients. Compressed tablets can be prepared by compressing, in a suitable machine, the compound in a free-flowing form, such as a powder or granules optionally mixed with a binding agent, lubricant, inert diluent and/or surface active/dispersing agent(s). Molded tablets can be made by molding, in a suitable machine, the powdered compound moistened with an inert liquid diluent.

Tablets of the present invention can also be coated with a conventional coating material such as Opadry™ White YS-1-18027A (or another color) and the weight fraction of the coating can be about 3% of the total weight of the coated tablet. The compositions of the present invention can be formulated so as to provide quick, sustained or delayed release of the compositions after administration to the patient by employing procedures known in the art.

When the excipient serves as a diluent, it can be a solid, semi-solid or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), soft and hard gelatin capsules and sterile packaged powders.

Tablet forms can include, for example, one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents and pharmaceutically compatible carriers. Such tablets may also comprise film coatings, which dissolve upon oral ingestion or upon contact with diluent.

In one embodiment of the present invention, the manufacturing processes may employ one or a combination of methods including: (1) dry mixing, (2) direct compression, (3) milling, (4) dry or non-aqueous granulation, (5) wet granulation, or (6) fusion. Lachman et al., *The Theory and Practice of Industrial Pharmacy* (1986).

In another embodiment of the present invention, solid compositions, such as tablets, are prepared by mixing a therapeutic agent of the present invention with a pharmaceutical excipient to form a solid preformulation composition containing a homogeneous mixture of the therapeutic agent and the excipient. When referring to these preformulation compositions(s) as homogeneous, it is meant that the therapeutic agent is dispersed evenly throughout the composition so that the composition may be readily subdivided into equally effective unit dosage forms, such as tablets, pills and capsules. This solid preformulation is then subdivided into unit dosage forms of the type described herein.

Compressed tablets are solid dosage forms prepared by compacting a formulation containing an active ingredient and excipients selected to aid the processing and improve the properties of the product. The term "compressed tablet" generally refers to a plain, uncoated tablet for oral ingestion, prepared by a single compression or by pre-compaction tapping followed by a final compression.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. A variety of materials can be used for such enteric layers or coatings, including a number of polymeric acids and mixtures of polymeric acids with such materials as shellac, cetyl alcohol and cellulose acetate.

The term "suspension tablets" as used herein refers to compressed tablets which rapidly disintegrate after they are placed in water, and are readily dispersible to form a suspension containing a precise dose of the compositions(s). Croscarmellose sodium is a known disintegrant for tablet formulations, and is available from FMC Corporation, Philadelphia, Pa. under the trademark Ac-Di-Sol®. It is frequently blended in compressed tableting formulations either alone or in combination with microcrystalline cellulose to achieve rapid disintegration of the tablet.

Microcrystalline cellulose, alone or co-processed with other ingredients, is also a common additive for compressed tablets and is well known for its ability to improve compressibility of difficult to compress tablet materials. It is well known in the art that commercially available products are available and can be used with the present invention. One example is available under the Avicel® trademark. Two different Avicel® products are utilized, Avicel® PH which is microcrystalline cellulose, and Avicel® AC-815, a co-processed spray dried residue of microcrystalline cellulose and a calcium-sodium alginate complex in which the calcium to sodium ratio is in the range of about 0.40:1 to about 2.5:1. While AC-815 is comprised of 85% microcrystalline cellulose (MCC) and 15% of a calcium-sodium alginate complex, for purposes of the present invention this ratio may be varied from about 75% MCC to 25% alginate up to about 95% MCC to 5% alginate. Depending on the particular formulation and active ingredient, these two components may be present in approximately equal amounts or in unequal amounts, and either may comprise from about 10% to about 50% by weight of the tablet.

Dry oral formulations can contain such excipients as binders (for example, hydroxypropylmethylcellulose, polyvinyl pyrilodone, other cellulosic materials and starch), diluents (for example, lactose and other sugars, starch, dicalcium phosphate and cellulosic materials), disintegrating agents (for example, starch polymers and cellulosic materials) and lubricating agents (for example, stearates and talc).

Since the tablet may be used to form rapidly disintegrating chewable tablets, lozenges, troches or swallowable tablets; the intermediate formulations, as well as the process for preparing them, provide additional aspects of the present invention.

Effervescent tablets and powders are also prepared in accordance with the present invention. Effervescent salts have been used to disperse medicines in water for oral administration. Effervescent salts are granules or coarse powders containing a medicinal agent in a dry mixture, usually composed of sodium bicarbonate, citric acid and tartaric acid.

When the salts are added to water, the acids and the base react to liberate carbon dioxide gas, thereby causing "effervescence."

The method of preparation of the effervescent granules of the present invention employs three basic processes: wet granulation, dry granulation and fusion. The fusion method is used for the preparation of most commercial effervescent powders. It should be noted that, although these methods are intended for the preparation of granules, the formulations of effervescent salts of the present invention could also be prepared as tablets, according to well-known prior art technology for tablet preparation.

Wet granulation is the oldest method of granule preparation. The individual steps in the wet granulation process of tablet preparation include milling and sieving of the ingredients, dry powder mixing, wet massing, granulation and final grinding.

Dry granulation involves compressing a powder mixture into a rough tablet or "slug" on a heavy-duty rotary tablet press. The slugs are then broken up into granular particles by a grinding operation, usually by passage through an oscillation granulator. The individual steps include mixing of the powders, compressing (slugging) and grinding (slug reduction or granulation). No wet binder or moisture is involved in any of the steps.

In another aspect, the present invention is directed to therapeutic methods of treating a condition or disorder where treatment with a liver X receptor alpha is indicated, the method comprises the oral administration of one or more compositions of the present invention to a subject in need thereof. In one embodiment, the condition or disorder is a vascular disorder or a neurodegenerative disorder.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The pharmaceutically acceptable carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such a lecithin, by the maintenance of the required particle size in the case of a dispersion and by the use of surfactants. Carrier formulations suitable for oral, subcutaneous, intravenous, intramuscular, etc. can be found in *Remington's The Science and Practice of Pharmacy* (2000).

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dose could be dissolved in 1 ml of isotonic NaCl solution and either added to 1000 ml of hypodermic or intravenous fluid or injected at the proposed site of infusion, (see, for example, *Remington's Pharmaceutical Sciences,* 15th Edition, pages 1035–1038 and 1570–1580).

In other embodiments, one may desire a topical application of compositions disclosed herein. Such compositions may be formulated in creams, lotions, solutions, gels, pastes, powders, or in solid form depending upon the particular application. The formulation of pharmaceutically acceptable carriers for topical administration is well known to one of skill in the art.

In another embodiment of the present invention, the therapeutic agent is formulated as a transdermal delivery device ("patches"). Such transdermal patches may be used to provide continuous or discontinuous infusion of the compounds of the present invention in controlled amounts. The construction and use of transdermal patches for the delivery of pharmaceutical agents is well known in the art. See, for example, U.S. Pat. No. 5,023,252, issued Jun. 11, 1991. Such patches may be constructed for continuous, pulsatile, or on demand delivery of pharmaceutical agents.

Other delivery systems can include time-release, delayed release or sustained release delivery systems. Such systems can avoid repeated administrations of the therapeutic agents of the present invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di- and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. Nos. 4,748,034 and 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

Use of a long-term sustained release implant may be suitable for treatment of cholesterol-related disorders in patients who need continuous administration of the compositions of the present invention. "Long-term" release, as used herein, means that the implant is constructed and arranged to deliver therapeutic levels of the active ingredients for at least 30 days, and preferably 60 days. Long-term sustained release implants are well known to those of ordinary skill in the art and include some of the release systems described above.

In another embodiment of the present invention, the compound for treating high cholesterol comes in the form of a kit or package containing one or more of the therapeutic compounds of the present invention. These therapeutic compounds of the present invention can be packaged in the form of a kit or package in which hourly, daily, weekly, or monthly (or other periodic) dosages are arranged for proper sequential or simultaneous administration. The present invention further provides a kit or package containing a plurality of dosage units, adapted for successive daily administration, each dosage unit comprising at least one of the therapeutic compounds of the present invention. This drug delivery system can be used to facilitate administering any of the various embodiments of the therapeutic compounds of the present invention. In one embodiment, the system contains a plurality of dosages to be to be administered daily or weekly. The kit or package can also contain the agents utilized in combination therapy to facilitate proper administration of the dosage forms. The kits or packages also contain a set of instructions for the subject.

Without further elaboration, it is believed that one skilled in the art, based on the description herein, can utilize the present invention to its fullest extent. All publications recited herein are hereby incorporated by reference in their entirety. The following specific examples, which describe synthesis and biological testing of several compounds of this invention, are therefore to be construed as merely illustrative, and not limitative of the remainder of the disclosure in any way whatsoever.

EXAMPLE 1

Synthesis of N-methyl-N-methoxy-3α,6α-dihydroxy-5β-cholanoic acid-24-amide (hypocholamide)

Into 300 mL 1,4-dioxane on ice was added 50 g of 3α,6α-dihydroxy-5β-cholanoic acid. Into the 1,4-dioxane solution was then dropwise added 15 mL ethylchloroformate the stirring, followed by addition of 30 mL triethylamine. The temperature of the solution thus obtained was raised to 20° C. and then stirred for 30 minutes. After that, 15 g of N,O-dimethylhydroxyamine hydrochloride was added into the solution, which was then stirred for another 30 minutes before 20 mL of 1 N NaOH solution was added to it. The solution was stirred for additional 16 hours. For work-up, the reaction solution was poured into 2000 mL 1N HCl on ice, followed by extraction with ethylacetate. The ethylacetate layer was washed in sequence, with 1N HCl, water, 1N NaOH, and water; and was then dried over anhydrous $MaSO_4$. The ethylacetate solvent was removed under reduced pressure. The residue was purified with a silica gel column to give pure hypocholamide in white foam at a 75% yield.

$^1$H NMR ($CDCl_3$): 4.07 (m, 1H); 3.70 (s, 3H); 3.62 (m, 1H); 3.18 (s, 3H); 1.05–2.50 (m, 26H); 0.92–0.95 (m, 3H); 0.91 (s, 3H); 0.65 (s, 3H). $^{13}$C NMR: 171.0, 71.6, 68.1, 61.2, 56.1, 55.4, 48.5, 42.8, 39.9, 39.8, 35.9, 35.5, 35.0, 34.8, 30.6, 30.2, 29.2, 28.8, 28.1, 24.2, 23.5, 20.7, 18.4, 12.0, 8.0.

EXAMPLE 2

Synthesis of 3α,6α,24-trihydroxy-5β-24,24-di(trifluoromethyl)-cholestane (hypocholaride)

19.2 g of 3α,6α-dihydroxy-cholic acid was dissolved in 200 mL anhydrous methanol. To the solution was then added 0.4 g of p-toluenesulfonic acid. After stirring at room temperature overnight, the methanol solvent was removed under reduced pressure to give a crude product (i.e., 3α,6α-dihydroxy-cholic acid methyl ester) in white foam.

Crude 3α,6α-dihydroxy-cholic acid methyl ester was then dissolved in 90 mL dimethylforamide (DMF). Into the DMF solution thus obtained was added 21.3 g TBDMS-Cl (1.5 eq.) and 24.0 g (3.75 eq.). The mixture was subsequently heated at 90° C. for 1 hour for protection of the 3α,6α hydroxy groups. The DMF solvent was subsequently removed under vacuum and the residue was added into ethyl ether and washed with sodium hydrogen carbonate and brine sequentially. After being dried over anhydrous sodium sulfate, ethyl ether was removed under reduced pressure. The residue was purified by a silica gel column to give a pure hydroxy-protected product in white foam at a 95% yield.

6.5 g of the hydroxy-protected product thus obtained was first dissolved in 60 mL glycol dimethyl ether. To the solution thus obtained were then added 1.5 mL trimethyl (trifluoromethyl)silane and a catalytic amount of CsF at room temperature. After stirring overnight, ethanol was added to the solution. The solution was then stirred at room temperature for 1 hour before all the solvents were removed under reduced pressure to give crude product (i.e., trifluoromethylketone).

The crude trifluoromethylketone product was dissolved in 60 mL glycol dimethyl ether. Into the solution were then added 1.5 mL trimethyl(trifluoromethyl)silane and a catalytic amount of CsF at room temperature. After the solution was stirred overnight, 3 mL ethanol was added to it. The solution was then further stirred at room temperature for 1 hour before all the solvents were removed under reduced pressure. The residue thus obtained was dissolved in a mixture of 100 mL ethanol and 3 mL concentrated hydrogen chloride. The ethanol solution was stirred for 1 hour, and the solvent was then removed under reduced pressure. The residue was subject to column purification to give the product (i.e., hypocholaride) as a white solid.

$^1$H NMR (CD$_3$OD): 4.00 (m, 1H); 3.50 (m, 1H); 0.92~1.89 (m, 32 H); 0.67 (s 3H). $^{13}$C NMR: 123.6 (dd, 280 Hz); 76.0 (m); 70.9; 67.1, 56.1, 55.7, 42.5, 39.8, 39.7, 35.8, 35.4, 35.3, 34.7, 34.0, 29.6, 28.5, 27.6, 23.7, 22.6, 20.4, 17.3.

EXAMPLE 3

Evaluation of Liver X Receptor Agonistic Activity

The liver X receptor agonistic activity of hypocholamide and hypocholaride was evaluated in a gene transactivation assay. See, e.g., Song, C. et al., *Steroids*, 2000, 65, 423–427.

Specifically, human embryonic kidney 293 cells were seeded into a 48-well culture plate at 10$^5$ cells per well in a Dulbecco's modified Eagle's medium (DMEM) supplemented with 10% fetal bovine serum. After incubation for 24 hours, the cells were transfected by the calcium phosphate coprecipitation method with 250 ng of a pGL3/UREluc reporter gene that consisted of three copies of AGGTCAagccAGGTCA fused to nucleotides −56 to +109 of the human c-fos promoter in front of the firefly luciferase gene in the plasmid basic pGL3 (Promega, Madison, Wis.), 40 ng pSG5/hRXR$_\alpha$, 40 ng pSG5/rUR or CMX/hliver X receptor$\alpha$, 10 ng pSG5/hGrip1, 0.4 ng CMV/R-luc (transfection normalization reporter, Promega) and 250 ng carrier DNA per well. See, e.g., Janowski, B. A. et al., *Nature*, 1996, 383, 728–731; Song, C. et al., *Endocrinology*, 2000, 141, 4180–4184; Hong, H. et al., *Proc. Natl. Acad. Sci. USA*, 1996, 93, 4948–4952; and Amemiya-Kudo, M. et al., *J Biol. Chem.*, 2000, 275, 31078–31085.

After incubation for another 12 to 24 hours, the cells were washed with phosphate buffer saline and then refed with DMEM supplemented with 4% delipidated fetal bovine serum. An ethanol solution containing hypocholamide or hypocholaride was added in duplicate to the DMEM cell culture with the final concentration of hypocholamide of 1 to 10 μM and the final ethanol concentration of 0.2%. After incubation for another 24 to 48 hours, the cells were harvested and the luciferase activity was measured with a commercial kit (Promega Dual luciferase II) on a Monolight luminometer (Becton Dickenson, Mountain View, Calif.).

The results show that both hypocholamide and hypocholaride were unexpectedly potent agonists of liver X receptor alpha and liver X receptor beta (i.e., UR). For instance, hypocholaride had ED$_{50}$ values of 20 nM and 80 nM for liver X receptor alpha and liver X Receptor beta, respectively.

EXAMPLE 4

In Vitro Study on ApoE Gene Expression

Rat astrocyte cultures were prepared from the cerebral cortex of 1–2-day-old Harlan Sprague-Dawley neonatal rats (Harlan, Indianapolis, Ind.) according to a method described in LaDu et al., *J. Biol. Chem.*, 2000, 275 (43): 33974–80. The astrocyte cells were grown to 90% confluency before the initiation of experiments. The culture medium was changed to α-minimum essential medium containing N2 supplements (Life Technologies, Inc., Gaithersburg, Md.), to which hypocholamide (0.1 to 1 μM/L) was added in triplicates. After incubation for 48–72 hours, a conditioned medium was collected and mixed with a SDS loading buffer. Cells lysate was made in situ by adding a SDS loading buffer to the culture plates.

Western blot analysis was performed as described by LaDu et al., supra. Cell lysate and conditioned media were loaded on a 4–20% gradient SDS-polyacrylamide electrophoresis gel and transferred onto nitrocellulose membranes after electrophoresis. The membrane were stained with amino black briefly and de-stained in distilled water. After the protein staining patterns were scanned, the membranes were blocked with a phosphate-buffered saline solution containing 0.2% Tween 20 and 1% fat-free milk powder. The ApoE amount was detected by using anti-rat ApoE polyclonal antibodies, horseradish peroxidase-conjugated goat anti-rabbit IgG, a chmiliminescent substrate (Pierce, Rockford, Ill.) and X-ray films.

Compared with vehicle treatment, the administration of hypocholamide resulted in an unexpectedly significant increase in the amount of ApoE in both cell medium and lysate.

EXAMPLE 5

Animal Study on ApoE Gene Expression

Twenty LDL receptor null gene mice were fed with an atherogenic diet (15% fat, 0.2% cholesterol) and divided into 4 groups (5 each) for receiving, respectively, 0 (control), 25, 50, and 100 mg/kg body weight/day of hypocholamide dissolved in their drinking water which also contained 0.25% HPCD, for 2 weeks. At the end of the 2 weeks, the mice were sacrificed and various tissues (i.e., liver, brain, and intestine) were collected. The collected tissues were analyzed according to the method described in Example 4.

The results show that the groups treated with hypocholamide had a total serum cholesterol level much lower than that in the control group. It was also shown that hypocholamide induced ATP-binding cassette protein A1 (ABCA1), sterol-regulating enhancing region binding protein 1 (SREBP-1) and apoE expression in the central nerve system of LDL receptor null mice. In situ hybridization using anti-ApoE probe showed much more apoE mRNA in the brains of the treated mice than that in the untreated mice, especially in the region of hippocampus and cerebral cortex.

EXAMPLE 6

Animal Study on Atherosclerosis

Twenty 8-week-old male apoE null mice (backcrossed with C57BL/6 mice for more than 10 generations) purchased from Jackson Laboratories were housed in a temperature-controlled room with a 12-hour light-dark cycle. The mice were fed on a standard rodent diet (Purina Mills, St. Louis, Mo.) with 0.25% β-cyclodextrin (Acros Organics, Ceel, BELGIUM) added to the water. Among them, 10 mice were fed on water supplemented with 0.5mg/ml hypocholamide. All procedures performed on the mice were in accordance with the National Institutes of Health and institutional guidelines.

At 32 weeks of age, each of the mice was anesthetized, exsanguinated via the retro-orbital sinus, and perfused at physiological pressure via the left ventricle of the heart with an outflow in the right atrium with phosphate buffered saline (PBS) for 15 minutes and then another 20 minutes with 4% paraformaldehyde and 5% sucrose in PBS. Aortas used for immunohistochemistry were perfused with PBS alone. The upper half of the heart and the proximal aorta (including the brachiocephalic trunk, left carotid, and left subclavian) were embedded in OCT Compound (Sakura Finetek, Torrance, Calif.) and then frozen in a mixture of dry ice and 2-methylbutane. The frozen tissue was serially sectioned into 10-μm sections from the brachiocephalic trunk through the aortic root. Every 10th section was stained with hematoxylin and eosin, with the neighboring sections stained with oil red O and Harris' hematoxylin and counterstained with fast green, or with Gomori's trichrome acid fuchsin (GTAF). The lesion area was quantified by using digitally captured oil red O-stained sections in the brachiocephalic trunk 350 μm distal from the point at which the brachiocephalic trunk entered the aortic arch and in the aortic root at the site of the appearance of the coronary artery. The size of the lesion in the brachiocephalic trunk was determined as a percentage of the total lumen area. See, e.g., Nicoletti, A. et al., *J. Clin. Invest.*, 1998, 102, 910–918.

Atherosclerosis was quantified by use of OpenLab Software, version 1.7.6. For immunohistochemistry involving T cells, the slides were incubated overnight at 4° C. with purified anti-CD4 rat IgG (GK1.5, 1 μg/mL), rinsed, and incubated with secondary rat anti-IgG (10 μg/mL). The antigen-antibody binding was detected by an avidin-biotinylated horseradish peroxidase system (Vector Laboratories, Burlingame, Calif.) with diaminobenzidine (DAB, Vector Laboratories) and counterstained with hematoxylin.

Plasma lipid levels were determined as described in Cabana, V. G. et al., *J. Lipid Res.*, 1999, 40, 1090–1103. Plasma obtained at the time of euthanasia (150 to 250 μL) was fractionated on tandem Superose 6 fast protein liquid chromatography (FPLC) columns in 200 mmol/L sodium phosphate (pH 7.4), 50 mmol/L NaCl, 0.03% EDTA, and 0.02% sodium azide, and 400-μL fractions were collected. The amount of cholesterol in the even-numbered fractions was determined and expressed as micrograms cholesterol per milliliter of plasma. The area under the lipoprotein peaks was quantified by computer digitizer (SigmaScan, Scientific Measurement Systems, Jandel Scientific, Chicago, Ill.) and expressed as percentage of total area.

The results indicate that hypocholamide effectively slowed atherosclerosis at distal sites in apoE null mice.

OTHER EMBODIMENTS

A number of embodiments of the invention have been described. Nevertheless, it will be understood that various modifications may be made without departing from the spirit and scope of the invention. Accordingly, other embodiments are within the scope of the following claims, and as various changes can be made to the above compositions, formulations, combinations, and methods without departing from the scope of the invention, it is intended that all matter contained in the above description be interpreted as illustrative and not in a limiting sense. All patent documents and references listed herein are incorporated by reference.

What is claimed is:

1. A method of treating atherosclerosis in a subject in need thereof, comprising administering to the subject a compound of formula (I):

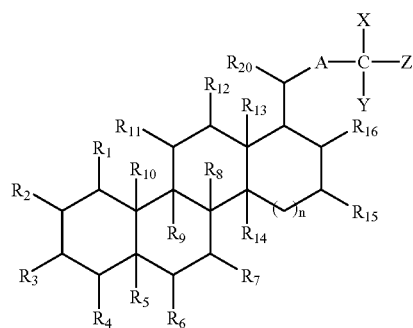

wherein
$R_1$, $R_2$, $R_4$, $R_5$, $R_7$, $R_{11}$, $R_{12}$, $R_{15}$, $R_{16}$, and $R_{20}$ are independently hydrogen, halo, alkyl, haloalkyl, hydroxy, amino, carboxyl, oxo, sulfonic acid, or alkyl that is optionally substituted at one or more positions with —NH—, —N(alkyl)-, —O—, —S—, —SO—, —SO$_2$—, —O—SO$_2$—, —SO$_2$—O—, —SO$_3$—O—, —CO—, —CO—O—, —O—CO—, —CO—NR'—, or —NR'—CO—;
each of $R_3$ and $R_6$ is hydroxy;
$R_8$, $R_9$, $R_{10}$, $R_{13}$, and $R_{14}$ are independently hydrogen, halo, alkyl, haloalkyl, hydroxyalkyl, alkoxy, hydroxy, or amino;
n is 0, 1, or 2;
A is alkylene, alkenylene, or alkynylene;
one of X, Y, and Z is OR', and the other two are independently $C_{1-8}$ haloalkyl; and
R' is hydrogen,
or a salt, an ester, an amide, an enantiomer, an isomer, a tautomer, or a polymorph thereof.

2. The method of claim 1, wherein $R_1$, $R_2$, $R_4$, $R_7$, $R_8$, $R_9$, $R_{11}$, $R_{12}$, $R_{14}$, $R_{15}$, and $R_{16}$ are independently hydrogen; $R_{10}$, $R_{13}$, and $R_{20}$ are independently alkyl; n is 0; and A is alkylene.

3. The method of claim 2, wherein $R_5$ is hydrogen.

4. The method of claim 3, wherein $R_5$ is beta-hydrogen; and $R_3$ and $R_6$ are alpha-hydroxy.

5. The method of claim 1, wherein $R_5$ is hydrogen.

6. The method of claim 5, wherein $R_5$ is beta-hydrogen; and $R_3$ and $R_6$ are alpha-hydroxy.

7. The method of claim 1, wherein X, Y, and Z, are independently trifluoromethyl or 3-chloropropyl.

8. The method of claim 7, wherein $R_1$, $R_2$, $R_4$, $R_7$, $R_8$, $R_9$, $R_{11}$, $R_{12}$, $R_{14}$, $R_{15}$, and $R_{16}$ are hydrogen; $R_{10}$, $R_{13}$, and $R_{20}$ are alkyl; n is 0; and A is alkylene.

9. The method of claim 8, wherein $R_5$ is hydrogen.

10. The method of claim 9, wherein $R_5$ is beta-hydrogen; and $R_3$ and $R_6$ are alpha-hydroxy.

11. The method of claim 7, wherein $R_5$ is hydrogen.

12. The method of claim 11, wherein $R_5$ is beta-hydrogen; and $R_3$ and $R_6$ are alpha-hydroxy.

13. The method of claim 1, wherein the compound is

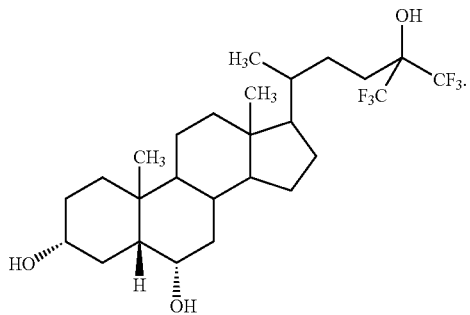

14. The method of claim 1, wherein two of X, Y, and Z, are independently trifluoromethyl.

15. The method of claim 14, wherein $R_1$, $R_2$, $R_4$, $R_7$, $R_8$, $R_9$, $R_{11}$, $R_{12}$, $R_{14}$, $R_{15}$, and $R_{16}$ are hydrogen; $R_{10}$, $R_{13}$, and $R_{20}$ are alkyl; n is 0; and A is alkylene.

16. The method of claim 15, wherein $R_5$ is hydrogen.

17. The method of claim 16, wherein $R_5$ is beta-hydrogen; and $R_3$ and $R_6$ are alpha-hydroxy.

18. The method of claim 14, wherein $R_5$ is hydrogen.

19. The method of claim 18, wherein $R_5$ is beta-hydrogen; and $R_3$ and $R_6$ are alpha-hydroxy.

20. The method of claim 1, wherein the compound of formula (I) is administered as a pharmaceutical composition comprising a therapeutically-effective amount of the compound of formula (I).

21. The method of claim 20, wherein the composition is a dosage form.

22. The method of claim 21, wherein the dosage form is selected from the group consisting of tablet, soft gelatin capsule, hard gelatin capsule, suspension tablet, effervescent tablet, powder, effervescent powder, chewable tablet, solution, suspension, emulsion, cream, gel, patch, and suppository.

23. The method of claim 20, wherein the composition comprises a pharmaceutically acceptable excipient.

24. The method of claim 23, wherein the pharmaceutically acceptable excipient comprises a binder, a disintegrant, a filler, a surfactant, a solubilizer, a stabilizer, a lubricant, a wetting agent, a diluent, a anti-adherent, a glidant, or a pharmaceutically compatible carrier.

25. A method for lowering blood serum cholesterol concentration in a subject in need thereof, comprising administering to the subject a compound of formula (I):

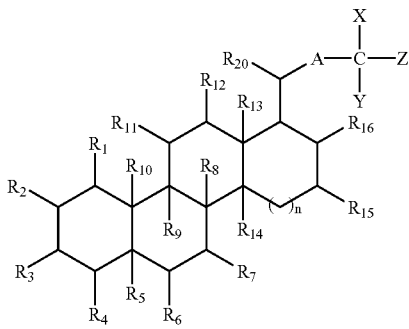

wherein $R_1$, $R_2$, $R_4$, $R_5$, $R_7$, $R_{11}$, $R_{12}$, $R_{15}$, $R_{16}$, and $R_{20}$ are independently hydrogen, halo, alkyl, haloalkyl, hydroxy, amino, carboxyl, oxo, sulfonic acid, or alkyl that is optionally substituted at one or more positions with —NH—, —N(alkyl)-, —O—, —S—, —SO—, —SO$_2$—, —O—SO$_2$—, —SO$_2$—O—, —SO$_3$—O—, —CO—, —CO—O—, —O—CO—, —CO—NR'—, or —NR'—CO—;

each of $R_3$ and $R_6$ is hydroxy;

$R_8$, $R_9$, $R_{10}$, $R_{13}$, and $R_{14}$ are independently hydrogen, halo, alkyl, haloalkyl, hydroxyalkyl, alkoxy, hydroxy, or amino;

n is 0, 1, or 2;

A is alkylene, alkenylene, or alkynylene;

one of X, Y, and Z is OR', and the other two are independently $C_{1-8}$ haloalkyl; and R' is hydrogen;

or a salt, an ester, an amide, an enantiomer, an isomer, a tautomer, or a polymorph thereof.

* * * * *